United States Patent [19]

Pollak et al.

[11] Patent Number: 4,813,416
[45] Date of Patent: Mar. 21, 1989

[54] BONDING ASSEMBLY AND METHOD FOR STERNUM CLOSING

[75] Inventors: Stanley B. Pollak, Huntington, N.Y.; William Blasnik, Englewood, N.J.

[73] Assignee: The Research Foundation of State University of New York, Albany, N.Y.

[21] Appl. No.: 27,302

[22] Filed: Mar. 18, 1987

[51] Int. Cl.⁴ .......... A61B 17/08/17/04; B65D 63/00; B65D 63/06
[52] U.S. Cl. ................ 128/335; 128/334 R; 128/92 YF; 128/92 R; 24/16 PB; 24/17 AP; 24/23 EE
[58] Field of Search ............... 24/20 S, 30.5 R, 30.5 P, 24/16 PB, 20 EE, 17 A, 23 EE; 128/335, 334 R

[56] References Cited

U.S. PATENT DOCUMENTS

| | | | |
|---|---|---|---|
| 268,632 | 12/1882 | Danforth | 128/335 |
| 380,093 | 3/1888 | Cruice et al. | 128/336 |
| 1,278,779 | 9/1918 | Springer | 24/17 A |
| 1,803,084 | 4/1931 | Wiziarde et al. | |
| 3,385,299 | 5/1968 | Le Roy | 128/335 |
| 3,802,438 | 4/1974 | Wolvek | 128/335 |
| 4,119,091 | 10/1978 | Partridge | 128/92 VZ |
| 4,201,215 | 5/1980 | Crossett et al. | 128/335 |
| 4,210,148 | 7/1980 | Stivala | 128/335 |
| 4,223,424 | 9/1980 | Burnett | 24/30.5 R |
| 4,279,248 | 7/1981 | Gabbay | 128/92 EA |
| 4,413,380 | 11/1983 | Suzuki | 24/30.5 P |
| 4,512,346 | 4/1985 | Lemole | 128/335 |
| 4,535,764 | 8/1985 | Ebert | 24/23 EE |
| 4,537,432 | 8/1985 | Meeks | 24/30.5 P |
| 4,583,541 | 4/1986 | Barry | 128/335 |
| 4,730,615 | 3/1988 | Sutherland et al. | 128/335 |

FOREIGN PATENT DOCUMENTS 427427  1/1967  Switzerland ............ 24/20 EE

Primary Examiner—Richard C. Pinkham
Assistant Examiner—Gary Jackson
Attorney, Agent, or Firm—Hoffmann & Baron

[57] ABSTRACT

A banding assembly with which sternum halves can be brought into abutting closure, the assembly including as a unitary arrangement, a needle for initiating passage of a band member connected at one end thereto around the sternum and there being a buckle connected to the band opposite end to allow for band loop formation and drawn tight enclosure of the sternum halves, the buckle and band embodying loop locking structure and excess band length being readily removable upon completion of the closure banding.

23 Claims, 4 Drawing Sheets

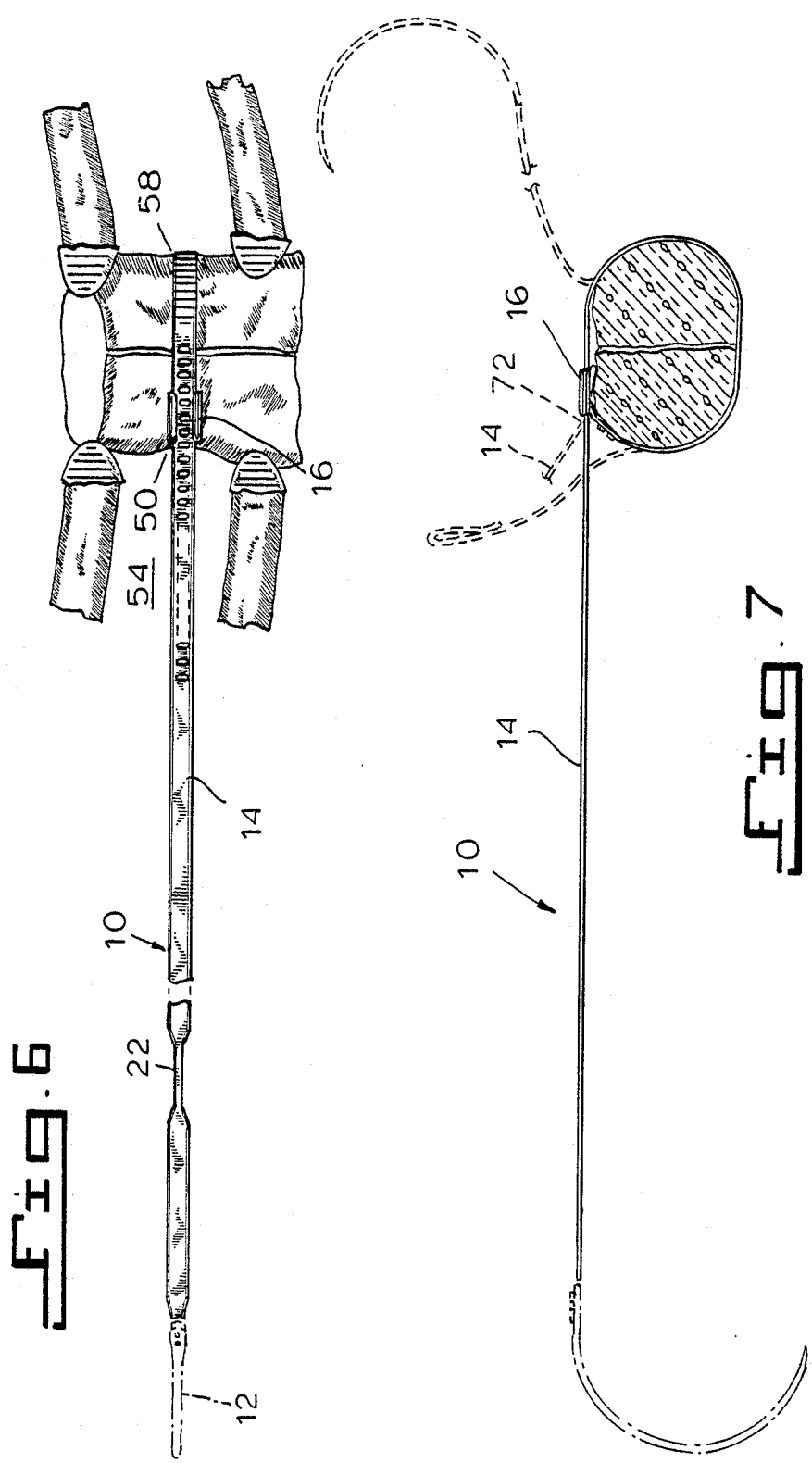

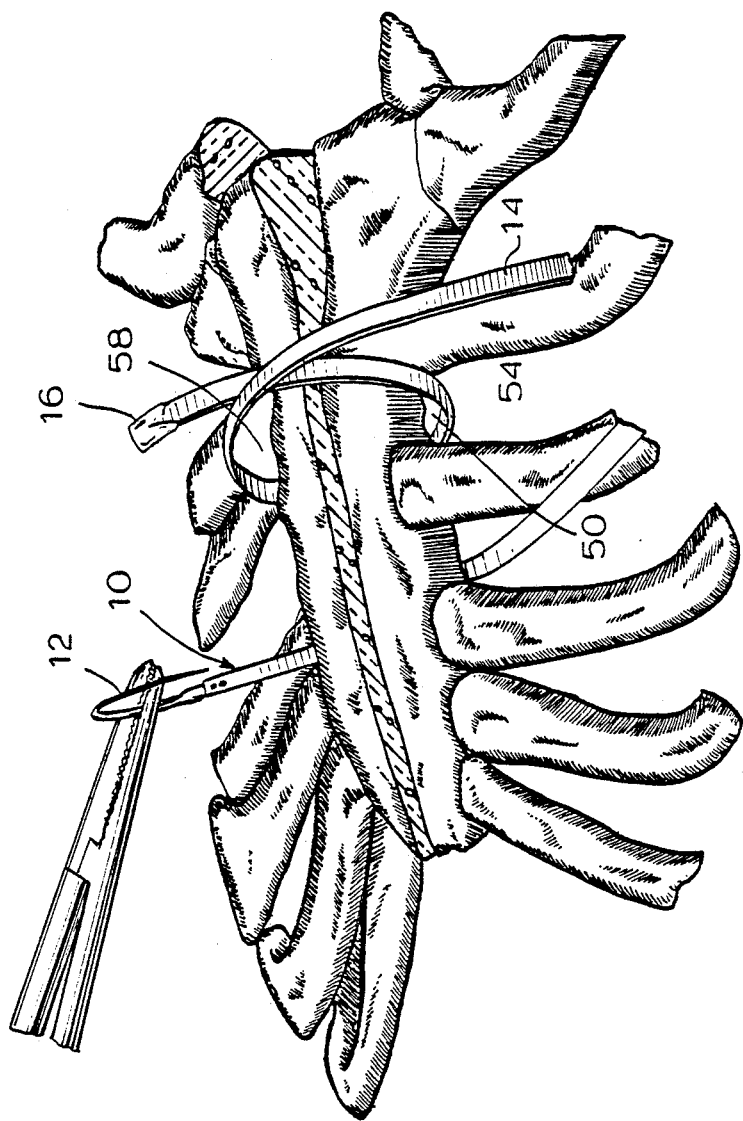

BONDING ASSEMBLY AND METHOD FOR STERNUM CLOSING

BACKGROUND OF THE INVENTION

The present invention relates to surgical devices and relates more particularly to a banding assembly for applying a clamp to close the split halves of the sternum incident surgery that involves a median sternotomy, e.g., open heart surgery.

For proper healing of the split sternum to occur the surgically opened faces must be approximated, compressed and held together rigidly. This task is complicated by the physiological role of the sternum. It is a functional component of the thoracic cage and, with the costal cartilages, serves as the hinge for the "bucket handle" action of the ribs during respiration. The incessant motion of the rib cage transmits continuous stresses across the sternum. Any method for closing the split sternum must be able to maintain compression and rigidity across the closure in the face of these constant stresses.

One commonly used technique closes the sternum with interrupted stainless steel wires. Five or six 20 gauge stainless steel wires are placed either parasternally (around the sternum) or transsternally (through the sternum) using a large, swaged-on cutting needle. The needles are cut off and the sternal halves are approximated by twisting the wires. Finally the wires are cut short and the ends are tucked into the adjacent tissue. While this is a useful surgical technique for closing the sternum, there are certain problems associated with this procedure. The wires are difficult to place and if to be placed transsternally, the needle must be driven through the sternum, a physically very difficult task. The internal mammary artery can be easily injured when the wires are placed in the parasternal position by the cutting needles which are usually used although tapered needles would be more appropriate in this location. The internal mammary artery passes in close proximity to the area in the intercostal space through which the parasternal wire is passed and injuries to the internal mammary artery are not unusual following the use of cutting needles in this area. Also sharp wires can cause cutting of surgical gloves and injure the operator. Cutting the needle off of the wire creates a sharp point at the end of the wire. The presence of 10 to 14 of these sharp points in a field crowded with hand motion inevitably results in a certain number of cut gloves and also cut fingers with resultant risks to both patient and operator.

An additional problem is that the stress during twisting produces torsional stresses that severely weaken the wire and they often break during their application as they are given that final extra twist used to make the closure "extra snug." The stresses imparted by respiratory motion of the chest cage can further fatigue the wires and cause them to break during the post-operative period. Further, the ends of the twisted wires can often be felt by the patient below the skin. This can be a source of discomfort and concern for the patient. In the most extreme case of the problem the wires cause a mechanical irritation on the skin that can progress to the point where they actually erode through the skin and become infected. When this happens, the wires must be surgically removed.

A major disadvantage of using wires is that they can slice through thin or osteoporotic bone. When sternal wires are used in those older or female patients who have thin or osteoporotic bone they have a tendency to slice through the bone. The large amount of force that the wire applies over its small surface area causes the wire to crush the underlying bone. This occurs during the tightening of the wire and continues during each respiratory cycle until the tension on the wire is eased. When this happens the compression of the sternal closure rigidity is lost.

Finally it should be noted that closure of the sternum with wires is a slow and tedious technique.

Other techniques for closing the sternum have been proposed. For example, U.S. Pat. No. 4,583,541 while still employing wire banding, positions a board at the front of the sternum through which the wires are passed before knotting and the knots are placed in a groove in the board. U.S. Pat. No. 4,279,248 discloses use of C-shaped clamp placed at both sides of the sternum which are clamped together with a threaded screw passing through the sternum, the clamps biting into the bone to provide firm sternum halves closure. U.S. Pat. No. 4,201,215 discloses use of a two-piece C-shaped clamp at one side of the sternum, the clamp pieces having hook ends which pass around to the other side of the sternum. The clamp pieces are assembled and slid tight in opposite directions and crimped together to provide clamp together of the two parts of the sternum. The clamping pieces may be provided with tongue and recess means to lock them in a clamp position and the clamp pieces are then crimped together. Tools such as vise grip pliers must be used in this procedure to effect clamp crimping. U.S. Pat. No. 3,802,438 discloses sternum closure with wires in conjunction with a splice plate in which the wires are received. By use of special tools, the splice plate is deformed to anchor the wires therein and in the course of which the sternum is closed. The procedures and devices disclosed in these patents mitigate to a certain extent the problems discussed earlier such as perhaps those associated with patient discomfort caused by twisted wire ends. But they still rely on use of wires and because of the potential for wires to slice or invade the sternum and adjacent tissue structure it is easy to understand that sternum closure without employment of wires is to be preferred.

The sternal banding technique was developed to avoid some of the drawbacks of wire closure. Thus stainless steel bands popularly known as "Parham" bands have been used for closing the sternum as have nylon bands similar to the surgical bands disclosed in U.S. Pat. No. 4,119,091. But these forms of banding possess their own particular shortcomings.

SUMMARY OF THE INVENTION

Accordingly, it is an object of the invention to provide a banding assembly for applying a clamp to closingly abut the split halves of the sternum which is a major improvement over the twisted wire sternal closure and which avoids the problems found in other known sternal banding techniques.

Another object is to provide a banding assembly with which sternum band clamps can be placed more quickly and easily and therefore allowing for more rapid and carefully effected wound closure.

A further object is to provide a sternum banding assembly the use of which lessens the possibility of causing injury to the internal mammary artery during the sternum closing procedure.

A still further object is to provide a sternum banding assembly the use of which is characterized by absence of sharp end structure which could cause cuts to surgical gloves, operator's fingers and like risks.

Another object is to provide a sternum banding assembly which can be inserted and tightened with implements normally available in an operating room such as a Kocher clamp, a towel clamp etc. so there thus be no need to rely on availability of special tools.

Yet another object is to provide sternum closure which is stronger and more secure than found with use of prior closure techniques.

Still another object is to provide a banding assembly for applying a clamp to closingly abut the split halves of the sternum which effects sternum non-invasive compressive force distribution along an appreciable reach of the sternum, has a smooth low profile which serves to reduce certain wound problems and which as a result of its function of approximating the sternal halves more rigidly, promotes more rapid sternal healing.

In accordance with the invention, the banding assembly is provided as and comprises in elongate array form, the several components involved in applying a clamp to sternum halves to effect abutting closure thereof. These components include a curved surgical needle having such curved sweep thereto that it readily can be inserted at one parasternal location alongside the sternum to underpass same and emerge alongside the sternum at an opposite parasternal location. An elongated, thin flat stainless steel band is connected at one end to the needle so that it will follow the needle in underpass draw around the sternum posterior side and its said one end emerge at the said opposite parasternal location. The needle preferably is connected or joined with the band one end by frangible joint so that as soon as the needle has passed out at the other parasternal location and a working following length of the band has emerged, the surgeon can easily break off the needle from the band and remove it from the surgical field.

A buckle member is carried fixedly at the other end of the band. In the closure procedure, the sternum underpass band draw is effected to sufficient extent to present leading and trailing end lengths that can e temporarily folded across the topside or anterior of the sternum halves. The surgeon will then repeat the foregoing with additional banding assemblies until four or five have been inserted in the chest. It is only after all such banding assemblies have been thusly placed that the surgeon will form and tighten loops with the respective assemblies since once an assembly is tightened to proximate the sternum halves no further bands can be inserted. In forming the loop with the band of an assembly, the band will be inserted and pulled through a band guide and retaining slide through course in the buckle to form a closed loop about the sternum halves. By holding the buckle with one of the surgical implements commonly available in surgery, viz., a towel clamp, and grasping the working end of the band with another such implement, e.g., a Kocher clamp, the surgeon can draw the loop tight in encircling embrace about the two proximated sternum halves to compressively abut same together under holding constraint necessary to promote sternum healing and preclude wound dehiscenses while at the same time utilizing a clamp for that purpose which minimizes subsequent patient discomfort from its presence in his chest. Since the band is relatively wide as compared to its thickness, the compressive force applied by the tightened closed band loop to the sternum is well distributed along a appreciable reach of the sternum and in such manner as to be non-invasive and non-traumatizing of any thin or osteoporotic bone structure thereof.

To maintain the closed band loop in desired locked loop configuration and size, the band and buckle member are provided with cooperating locking means, such means being inoperable, i.e., it releases when the band is drawn in a loop draw tight direction but is operable to prevent any band movement in an opposite direction. Thus once the loop has been snugged tight around the sternum halves it becomes locked and cannot release. In one convenient form, the locking means is constituted of a plurality of slotted openings formed in the band and a projection carried in the buckle member structure. As the loop is being drawn tight by the surgeon, the slotted openings slide over the projection which is inclined in the draw tight direction, but once the band is in secured loop embrace of the sternum halves, any band slide movement opposite the draw tight direction is prevented by a secure engagement of the buckle member projection in a certain one of the band slotted openings.

The invention also provides that upon completion of the clamp application, the excess band length extending beyond the closed tight loop is removed and to facilitate such removal the band is transversely weakened with underscored groove structure or break notches at spaced locations therealong and arranged such that the break can be effected to coincide with an end of the buckle member so that no sharp edged structure protrudes from the clamp loop.

In the normal closure procedure a total of four or five such assemblies will be used to effectuate sternum closure with the respective clamps applied therewith disposed parasternally in the intercostal spaces of the chest cage and each loop formed and drawn tight as described above.

The invention accordingly comprises the features of construction, combination of elements, and arrangements of parts for effecting sternum closure which will be exemplified in the construction hereinafter set forth and the scope of the invention will be indicated in the claims.

BRIEF DESCRIPTION OF THE DRAWINGS

A fuller understanding of the nature and objects of the invention will be had from the following detailed description taken in conjunction with the accompanying drawings, in which:

FIG. 6 is a plan view illustrating the placement of a clamp with the assembly around the abutting sternum halves, the loop being shown in the draw tight locked position thereof and the clamp located in one of the intercostal spaces of the rib cage; and FIG. 7 is a elevational view of the FIG. 6 depiction; and FIG. 8 is a perspective view showing how the several banding assemblies are inserted in the chest loosely around the sternum halves preliminary to loop formations therewith and draw tight of the loops to affect the closure.

Throughout the following description, like reference numerals are used to denote like parts in the drawings.

DESCRIPTION OF THE PREFERRED EMBODIMENT

Figure 1:
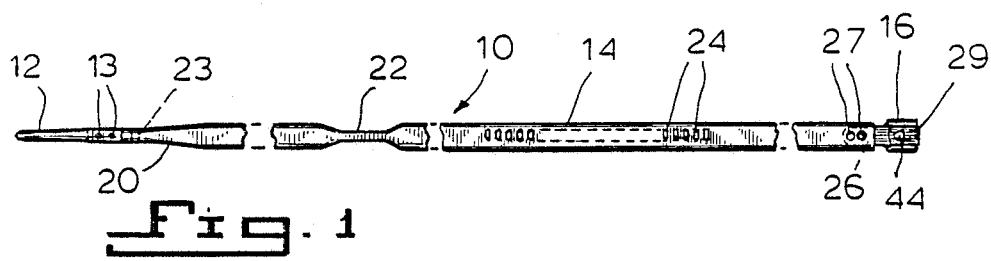
FIG. 1 is a top plan view on reduced scale of the banding assembly of the present invention, the length thereof being broken away at a number of locations.

Referring now to FIG. 1 of the drawings, the banding assembly 10 includes as connected together components, a surgical needle 12 connected to one end of elongated, thin and relatively wide flat band 14 and a buckle member 16 fixedly connected to the other end of band 14. The needle 12 will be configured in such manner as to facilitate the insertion thereof from one parasternal location, under the sternum halves and then outwardly at an opposite parasternal location. Advantageously, the needle will have a curved sweep as shown in FIGS. 6 and 7 and that sweep will dispose in a plane generally normally to that of band 14 as seen from FIG. 1. These components are made of biologically inert metallic materials, preferably stainless steel. The overall length of the assembly is about 14 inches, the buckle member having overall dimensions of about ¾ inch length by about ¼ inch width by about ⅛ inch height. The band width is about 0.18 inch and its thickness about 0.01 inch so that the band is readily pliable for assuming a sternum conformable encircling or loop course as will be described in detail below. The connection of the needle 12 and buckle member 16 to the opposite ends of band 14 can be by any means suited to that purpose such as riveting 13 or spot welding, but the joinder of the needle and one end of the band should be at a juncture embodying readily frangible structure so that following insertion of the needle at a parasternal location adjacent one side of the sternum and pass out from the sternum posterior side at an opposite parasternal location with follow-up pull through of the band, the needle can be broken off from the assembly and removed from the surgical field. One such form of weakened joint structure can be a transverse underscore cut or notch 23 formed in the said one end of band 14 immediately downstream of the point where rivets 13 pass through the band (FIG. 1). That break off can be effected by the surgeon with digitally applied back and forth bending of the needle relative to the band and for which purpose the surgeon may employ a pliers-like implement.

Band 14 can have a tapered fore end as at 20 to reduce tissue trauma, a section of diminished width as at 22 used for initiating band loop formation as will be explained later, and a plurality of band slotted openings 24 which are related to loop locking function and provided in such numbers as gives selection for employment of the banding assembly in connection with sternum closure of patients having sterna sizes which vary over any expected-to-be-encountered range of such sizes. The openings 24 in the depicted band embodiment are disposed proximate the other end of the band starting distant from the buckle member at about 3 inches, are placed on a pitch distance of about 0.09 inch, have an opening length of about 0.04 inch, opening width of about 0.08 inch and are present in a total number of twenty-one of such openings. The assembly is generally useable with sterna having circumferential lengths of about 3 to about 5 inches.

Figure 2:
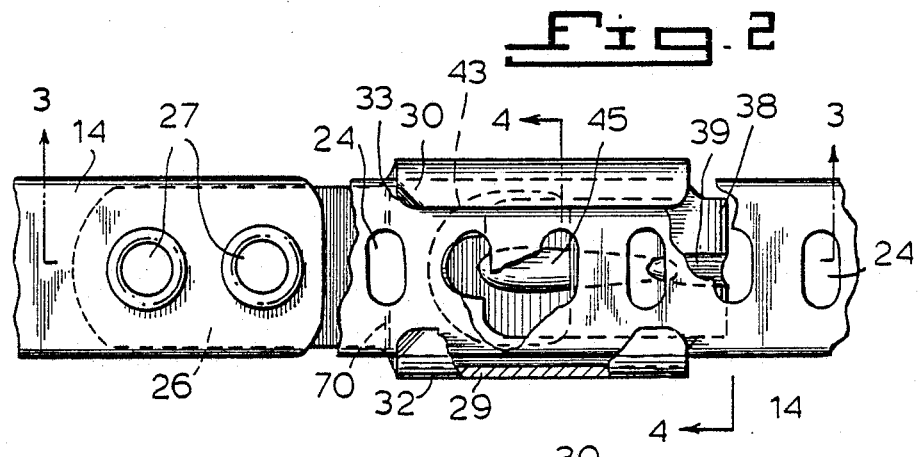
FIG. 2 is a fragmentary top plan view on enlarged scale of the buckle member which is connected to the rear end of the band and illustrating the manner in which the fore or working end of the band is received in the buckle member band guide and retaining slide course, the band locking means being depicted in the operable or locking condition thereof.
Figure 3:
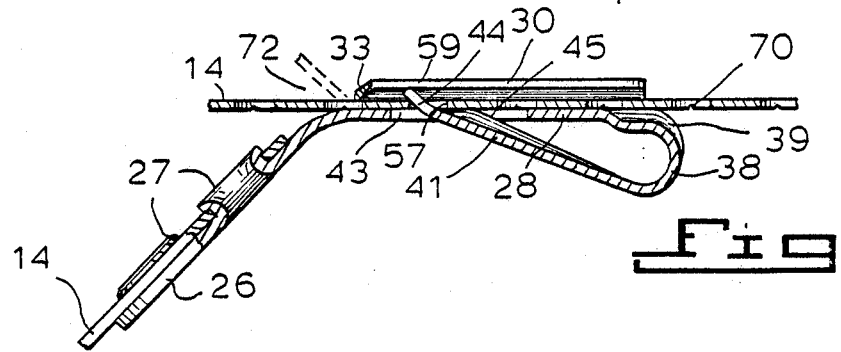
FIG. 3 is a sectional view as taken along the line 3—3 in FIG. 2.
Figure 4:
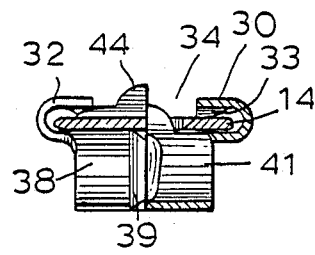
FIG. 4 is a sectional view as taken along the line 4—4 in FIG. 2.

Reference is had now to FIGS. 2-4 which detail more specific constructional features of the band 14 and buckle member 16. The buckle member 16 includes an anchor section 26 of flat span character on which the tail end of the band 14 is received and fixedly secured thereto by means of rivets 27 formed out of the anchor section structure and headed over on the band tail end as seen in FIGS. 2 and 3. Since the buckle member 16 is made of material substantially the same thickness as the band (about 0.01 inch), the anchor section 26 can readily be bent in the orientation shown in FIG. 3 relative to the remainder buckle member structure when conforming the band assembly to the sternum surface in loop encirclement in the manner to be described in greater detail later. The right side section 29 of the buckle member 16 presents structure which includes a saddle part 28 supportively receptive of the band when the latter is slid through the buckle member in forming a loop and that slide through course is defined by the saddle part and inturned flanges 30, 32 that confront spacedly with each other as shown to leave a space 34 (FIG. 4) between their facing inner edges, with the underfaces of the flanges being parallel spaced from the upper face of saddle part 28 and the flanges 30, 32 further functioning as band retainer means, with the fore ends of the flanges being crimped down as at 33 to guidingly engage the band.

The buckle member preferably is fabricated from a single metallic piece formed into its relative component configurations as shown. While the anchor section 26 and right side section 29 are shown having angulated relationship in FIGS. 2 and 3, it will be understood that is a relative positioning which exists following loop formation with the assembly. Prior to use of the assembly the said two sections are longitudinally aligned. Further integral structure of the buckle includes a hinge or loop segment 38 extending from saddle part 28 and formed with a stiffening loop rib 39, and a spring leaf 41 extending upwardly from the loop segment in passage through a slot 43 in the saddle part 28. The tip end of spring leaf 41 is laterally narrowed and inclined upwardly slightly relative to the remainder portion thereof so as to define a spring tooth or projection 44 with the remainder portion of the spring leaf having a stiffening leaf rib 45 formed therein.

Figure 3A:
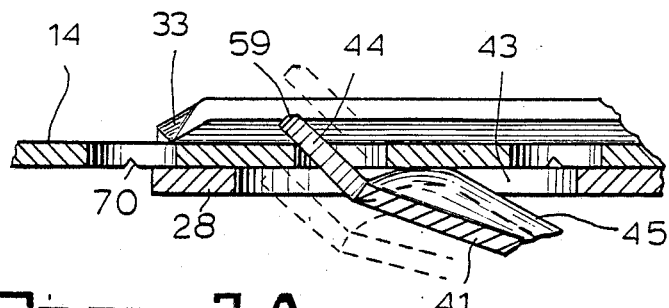
FIG. 3A is a fragmentary vertical central sectional view illustrating the operation of the band locking means.

FIGS. 2, 3 and 3A show how the band 14 is received on saddle part 28 and how the projection 44 thereon passes through in locked loop retaining function in one of the band slotted openings 24. This locked loop retaining function precludes opening of a formed loop in the band by any force as tends to slide the band rightwardly (as viewed in FIG. 3). On the other hand leftwise or loop tightening direction sliding of the band is possible since such band movement will cause the resiliently biased spring leaf 41 to yield downwardly freeing passage of the band over the projection 44. The loop locking functioning will be further apparent with reference to FIG. 3A. In that showing, the position of the spring leaf 41 (shown in full lines) is that where a sternum encircling band loop is locked, the projection 44 on the spring leaf is in band movement blocking presence in one of the band openings 24 and the stiffening leaf rib 45 is snubbed up against the underside of band 14. Sternum band loop loosening would require rightwardly sliding travel of band 14 and that it will be noted is not possible in this circumstance. Further sternum band loop tightening is of course possible (up to the point where such loop size corresponds to that needed for compressing together the sternum halves). Such loop tightening requires leftwise sliding movement of band 14. FIG. 3A shows in dashed lines two moved positions of the spring leaf 41. The upper dashed line showing is that occupied by the spring leaf when the band 14 has not been inserted in the buckle to form a band loop. The lower dashed line showing, however, is that associated with band loop tightening. When band 14 is slid leftwise to tighten the loop, the rear transverse edge 57 of the particular band slotted opening 24 in which spring tooth 44 is disposed will engage that tooth and cause downward springing of the spring leaf to thus clear the tooth from the slotted opening. The band 14 will continue to slide leftwise across the tip end of tooth 44 which is coined or chamfered as at 59 to facilitate such sliding, and until the next succeeding slotted opening 24 is situated where tooth 45 can spring up into that opening. But tooth retraction will commence anew as band leftwise sliding continues and this sequence will repeat until final loop dimension is achieved at which time loop locking by entry of the tooth into the requisite slotted opening will occur.

Figure 5:
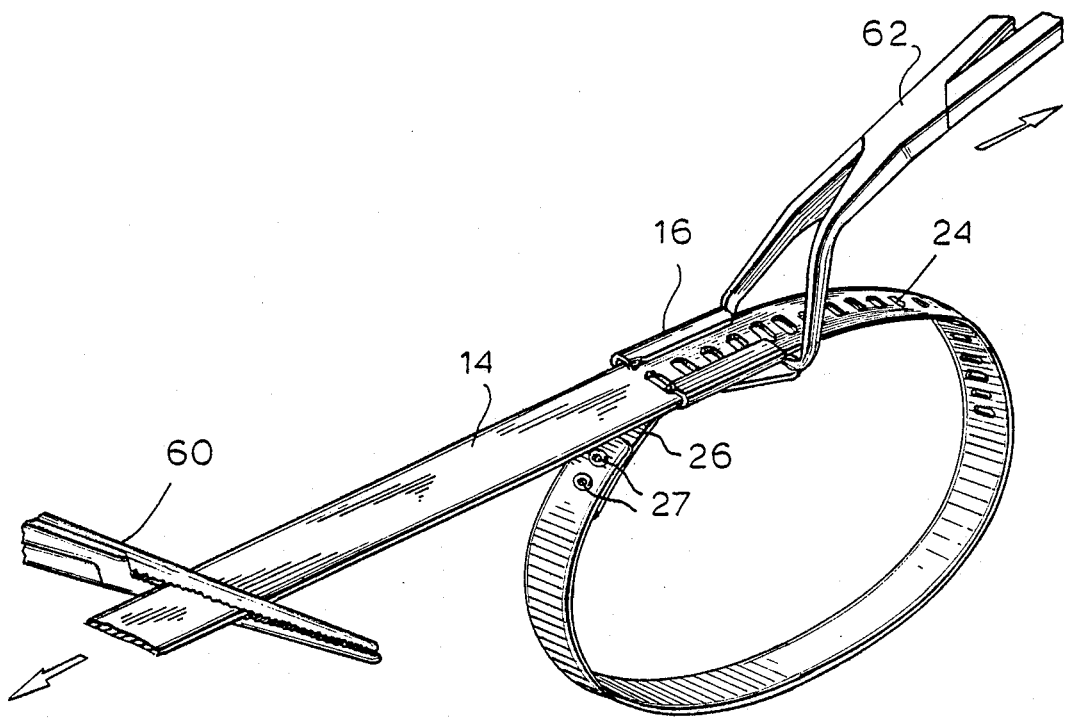
FIG. 5 is a perspective view illustrating the manner in which a closed loop is formed with the assembly and the draw tight procedure effected by the surgeon.

Further understanding of the banding assembly and the sternum clamp applied therewith will be had from the description now given of the use of same for effecting sternum closure and for that purpose reference being made to FIGS. 5–8. Upon completion of the surgical procedure that involved a median sternotomy, e.g., an open heart by-pass procedure, the surgeon will proceed to effect sternum closure and for which purpose an adequate quantity of sterile banding assemblies 10 will be available. Selecting a parasternal location 50 at one side of the sternum in an intercostal space 54, the surgeon will initiate a first assembly insertion by inserting the assembly curved needle 12 at location 50 to access the posterior of the sternum making an underpass course with the needle and directing it outwardly at the other side of the sternum as at location 58 and continuing an outdraw thereof from location 58 so that the fore end of the attached band 14 follows and emerges at location 58. In this respect it will be noted that FIGS. 5–7 depict the procedure where the surgeon initiates insertion at the right side of the sternum, whereas, FIG. 8 depicts that wherein insertion is initiated at the left side of the sternum. An intermediate positioning of the thus inserted assembly is shown in FIG. 7 in dashed lines. When a sufficient working length of the band has been drawn through that location 58, the surgeon can remove or separate the needle from the band by break force applied at the point of underscore notch 23, the removed needles being depicted in long and short dashed lines in FIGS. 6 and 7. Pull through of the band to an extent to allow draped foldover of the band as shown, e.g., in FIG. 8 is then completed by the surgeon. No loop formation or tightening will as yet occur inasmuch as once a clamp is formed and pulled tight causing abutment together of the sternum halves it would not be possible to insert additional bands. The surgeon now goes on to insert three or four more band assemblies in like manner. Once all these assembles are inserted in the draped over position of each, the surgeon will then proceed to form and tighten a closed loop in each band 14. This most conveniently can be done by side slipping the diminished width length 22 of band 14 through opening 34 in the buckle onto the saddle part 28 thereof to therewith position the band in the buckle member guide and retaining slide through course. By now effecting leftwise pull on the band, the wider width part thereof is brought under the retaining compass of flanges 30, 32 and pull is continued to close down the size of the formed loop. In doing this, the fore end of the band 14 may be gripped with a readily available surgical implement 60, e.g., a Kocher clamp and the buckle member 16 can be gripped and held with another readily available implement 62, a towel clamp, the jaw tips of which can be positioned in loop segment 38 of the buckle. By pulling in the draw tight direction with Kocher clamp 60 and holding the buckle member with clamp 62, and with the sternum halves proximated in abutment one with the other, the closed loop can be drawn tight compressively against the sternum halves to effect abutted closure thereof. When the loop is closed to snugged embrace about the sternum, the locking means provided by projection 44 and slotted openings 24 is operative to prevent band movement opposite to the draw tight direction and because of the large number of openings 24, the opening most accommodating of the encirclement dimension of the sternum will be cooperatively engaged by projection 44 so that a tight clamp together of the sternum halves is set and sustained thereafter. The surgeon then goes on to form a loop and tighten the loop in the three or four other assemblies previously inserted so that on conclusion a complete and absolutely reliable sternum closure has been made.

A particular advantage of the clamp applied in accordance with the invention is that the compressive force application involved in making healing promotive closure is uniformly distributed along an appreciable reach of the sternum and in band-sternum contact condition which is non-invasive and non-traumatizing of thin and osteoporotic bone. This is an effect in marked contrast with the potential for such adverse occurrence as is present where wire closure is employed and point concentration of compressive force is involved.

Once the clamp is in place, the excess working length of the band is removed. As shown in FIGS. 3 and 7, the band is transversely notched as at 70 in the marginal parts thereof adjacent each slotted opening 24. Thus by applying a pull-up force on the band at the left end of the buckle member right side section as at 72, the frangible character of the band allows ready separation of the excess length from the closed loop and this without leaving any sharp pointed residue in the clamp structure since the break point on the band is generally coincident with the left end of the buckle member right side section 29.

It will be seen from the foregoing that the present invention provides a significantly improved procedure for effective sternum closure. It offers the advantages over prior procedures of being more simple to effectuate, more rapidly carried out, less invasive of the patient's comfort during healing and produces a closure of optimized integrity.

While there is disclosed above only one embodiment of the banding assembly, it will be understood that those skilled in the art may make various modifications thereto while still remaining within the scope of the inventive concept disclosed.

What is claimed is:

1. For use following surgery that involves a median sternotomy, a banding assembly for applying a clamp to closingly abut the split halves of the sternum, the assembly comprising in elongate array the following components:

a surgical needle having a shape that renders it readily insertable from one parasternal location alongside the sternum to underpass the sternum halves and emerge alongside the sternum at an opposite parasternal location:

an elongated thin flat band, the needle being connected to one end of said band so that the band can be drawn in following underpass run of the sternum halves when the needle is withdrawn outwardly from said opposite parasternal location; and a buckle carried at the other end of said band, the buckle having a band guide and retaining slide through course for accommodating sliding pass through of the said one end of the band for establishing a closed band loop about the sternum halves which loop can be drawn tight to apply compressive clamp together force to bring the sternum halves into abutment, the band being relatively wide as compared to its thickness to effectuate a sterna non-invasive, non-traumatizing compressive force distribution along an appreciable reach of the sternum, said buckle band guide and retaining slide through course being defined by inturned buckle flanges arranged opposite each other, the band along an intermediate length portion being demarked by a section of diminished width to facilitate insertion of said band into the slide through course by entry passage of said intermediate portion through the space between the confronting flanges for effecting formation of a closed loop with the band, the buckle and the band carrying cooperating loop locking means being inoperable when the band is drawn in a loop draw tight direction but operable to loop lock the band preventing any movement thereof in an opposite direction and thereby sustaining set the looped compressive embrace of the abutting sternum halves.

2. The banding assembly of claim 1 in which the surgical needle has a curved shape the curved sweep of which lies within a plane normal to the plane of the band.

3. The banding assembly of claim 1 in which the joinder location of the needle and said one band end is characterized by a weakened, readily frangible structure provided such that upon band underpass of the sternum and outdraw thereof from said other parasternal location, break force can be applied to separate said needle from said band.

4. The banding assembly of claim 3 in which the needle-band joinder structure is weakened by a transverse underscore notching of such structure.

5. The banding assembly of claim 1 in which the buckle-band loop locking means comprises a projection on the one and a plurality of spaced slotted openings in the other in which said projection can engage.

6. The banding assembly of claim 5 in which the band includes transversely weakened structure therein at longitudinally spaced locations therein for readily frangibly separating band excess length run from the drawn tight end of said buckle member along a desired weakened structure location generally coincident with the end of the buckle member, so that following separation of the excess band length run at said desired weakened structure location, no appreciable remainder band length extends beyond said buckle end, thereby avoiding sharp edged structure protrusion from the closed clamp loop.

7. The banding assembly of claim 6 in which the weakened structure is defined by transverse break notches formed in the band.

8. The banding assembly of claim 7 in which the break notches extend in marginal structure at opposite sides of the slotted openings.

9. A banding assembly for use following surgery involving a median sternotomy, and for applying a clamp to closingly abut the split halves of the sternum, the banding assembly comprising in elongated array the following components:

a surgical needle having a shape that renders it readily insertable from one parasternal location alongside the sternum to underpass the sternum halves and emerge alongside the sternum at an opposite parasternal location;

an elongated thin flat band, the needle being connected to one end of said band so that the band can be drawn in following underpass run of the sternum halves when the needle is withdrawn outwardly from said opposite parasternal location; and a buckle carried at the other end of said band, the buckle having a band guide and retaining slide through course for accommodating sliding pass through of the said one end of the band for establishing a closed band loop about the sternum halves which loop can be drawn tight to apply compressive clamp together force to bring the sternum halves onto abutment, the band being relatively wide as compared to its thickness to effectuate a sterna non-invasive, non-traumatizing compressive force distribution along an appreciable reach of the sternum, the buckle and the band carrying cooperating loop locking means inoperable when the band is drawn in a loop draw tight direction but operable to loop lock the band preventing any movement thereof in an opposite direction and thereby sustaining set the looped compressive embrace of the abutting sternum halves, said buckle-band loop locking means including a projection on the on and a plurality of spaced slotted openings in the other in which said projection can engage.

said buckle including a longitudinal saddle part and flanges inturned from the margins of said saddle spaced from said needle and therewith defining the band guide and retaining slide through course, the projection being carried on a spring leaf extending upwardly through an opening in the saddle, the slotted openings being disposed in a section of said band proximate the said other end thereof and being present in a sufficient number thereof to allow for engagement of said buckle projection therewith over a range of tight closed loop sizes in correspondence to use of the assembly with sterna having different sizes.

10. The banding assembly of claim 9 in which the projection being carried on said spring leaf is inclined in the band loop tightening direction, whereby during band movement in loop tightening direction, such movement causes the spring leaf to yield freeing engagement of the projection with the slotted openings.

11. The banding assembly of claim 9 in which the slotted openings are uniformly spaced one from another along said band section.

12. The banding assembly of claim 11 in which the slotted openings are uniformly spaced on a centerline distance about 0.090" one from another.

13. The banding assembly of claim 9 in which the band includes transversely formed break notches formed adjacent opposite sides of the slotted openings, said slotted openings being sized such and the notches disposed such in the band that the band excess can be frangibly separated at the loop draw tight end of said buckle along a desired break notch generally coinciding with the end of the buckle member, whereby following separation of the excess band run at said desired break notch, no appreciable remainder band length part extends beyond said buckle end thereby avoiding sharp edged structure protrusions from the closed clamp loop.

14. The banding assembly of claim 13 in which the buckle further includes downwardly turned ends formed on the fore ends of the flanges of the buckle on the loop tight end thereof.

15. For use in a surgical procedure that involves approximating separated parts of an osseous structure, a banding assembly for applying a clamp to closingly abut the parts of the structure, the assembly comprising in elongate array the following components:
a surgical needle having a shape that renders it readily insertable from one location alongside the structure to surround structure parts and emerge alongside the structure at an opposite location;
an elongated thin flat band, the needle being connected to one end of said band so that the band can be drawn in following surrounding run of the structure when the needle is withdrawn outwardly from said opposite location; and
a buckle carried at the other end of said band, the buckle having a band guide and retaining slide through course for accommodating sliding pass through of the said one end of the band for establishing a closed band loop about parts which loop can be drawn tight to apply compressive clamp together force to bring the parts into approximating abutment, the band being relatively wide as compared to its thickness to effectuate a non-invasive, non-traumatizing compressive force distribution along an appreciable reach of the structure,
said buckle band guide and retaining slide through course being defined by inturned buckle flanges arranged opposite each other, the band along an intermediate length portion being demarked by a section of diminished width to facilitate insertion of said band into the slide through course by entry passage of the said intermediate length portion through the space between the confronting flanges for effecting formation of a closed loop with the band,
the buckle and the band carrying cooperating loop locking means inoperable when the band is drawn in a loop draw tight direction but inoperable to loop lock the band preventing any movement thereof in an opposite direction thereby sustaining set the looped compressive embrace of the structure parts.

16. For use following surgery that involves a median sternotomy, a banding assembly for applying a clamp to closingly abut the split halves of the sternum, the assembly comprising in elongate array the following components:
a surgical needle having a shape that renders it readily insertable from one parasternal location alongside the sternum to underpass the sternum halves and emerge alongside the sternum at an opposite parasternal location;
an elongated thin flat band, the needle being connected to one end of said band so that the band can be drawn in following underpass run of the sternum halves when the needle is withdrawn outwardly from said opposite parasternal location; and
a buckle carried at the other end of said band, the buckle having a band guide and retaining slide through course for accommodating sliding pass through of the said one end of the band establishing a closed band loop about the sternum halves which loop can be drawn tight to apply compressive clamp together force to bring the sternum halves into abutment, the band being relatively wide as compared to is thickness to effectuate a sterna non-invasive, non-traumatizing compressive force distribution along an appreciable reach of the sternum,
said buckle band guide and retaining slide through course being defined by inturned buckle flanges arranged opposite each other, the band along an intermediate length portion being demarked by a section of diminished width to facilitate insertion of said band into the slide through course by entry passage of the said portion through the space between the confronting flanges for effecting formation of a closed loop with the band,
the buckle having a buckle holding means for holding the buckle during approximations of the sternum halves, the buckle holding means allowing for the positioning of the jaw tips of a surgical implement therein,
the buckle and the band carrying cooperating loop locking means being inoperable when the band is drawn in a loop draw tight direction but operable to loop lock the band preventing any movement thereof in an opposite direction and thereby sustaining set the looped compressive embrace of the abutting sternum halves.

17. The banding assembly of claim 16, in which the band includes transversely weakened structure therein at longitudinally spaced locations therein for readily frangibly separating band excess length run from the drawn tight end of said buckle member along a desired weakened structure location generally coincident with the end of the buckle member, so that following separation of the excess band length run at said desired weakened structure location, no appreciable remainder band length extends beyond said buckle end, thereby avoiding sharp edged structure protrusion from the closed clamp loop.

18. The banding assembly of claim 17 in which the weakened structure is defined by transverse break notches formed in the band.

19. The banding assembly of claim 18 in which the break notches extend in band marginal structure at opposite sides of the slotted openings.

20. The banding assembly of claim 18 in which the buckle holding means comprises a loop segment which allows for the positioning of the jaw tips of a surgical implement therein.

21. A method for closing the split halves of a sternum following surgery involving a median strenotomy, said method comprising the steps of:

(a) providing a banding assembly which includes, in an elongate array, a surgical needle having a shape that renders it readily insertable from one parasternal location alongside the sternum to underpass the sternum halves and emerge alongside the sternum at an opposite parasternal location, an elongated thin flat band, the needle being connected to one end of the said band so that the band can be drawn in following underpass run of the sternum halves when the needle is withdrawn outwardly from said opposite parasternal location, a buckle carried at the other end of said band, the buckle having a band guide and retaining slide through course for accommodating sliding pass through of the said one end of the band for establishing a closed band loop about the sternum halves which loop can be drawn tight to apply compressive clamp together force to bring the sternum halves into abutment, the band being relatively wide as compared to its thickness to effectuate a sterna non-invasive, non-traumatizing compressive force distribution along an appreciable reach of the sternum, said buckle band guide and retaining slide through course is defined by inturned buckle flanges spaced confrontingly one with the other, the band along an intermediate length portion being demarked by lateral width diminution to facilitate sidewise insertion of said band into slide through course by entry passage of the said portion through the space between the confronting flanges for effecting formation of a closed loop with the band, the band including transversely weakened structure therein at longitudinally spaced locations therein for readily frangibly separating band excess length run from the drawn tight end of said buckle along a desired weakened structure location generally coincident with the end of the buckle, so that following separation of the excess band length run at said desired weakened structure location, no appreciable remainder band length extends beyond the buckle, thereby avoiding sharp edged structure protrusion from the closed clamp loop, the buckle having a buckle holding means for holding the buckle during approximation of the sternum halves, the buckle holding means including jaw tip receiving means and allowing for the positioning of the jaw tips of a surgical implement therein, the buckle and the band carrying cooperating loop locking means inoperable when the band is drawn in a loop draw tight direction but operable to loop lock the band preventing any movement thereof in an opposite direction and thereby sustaining set the looped compressive embrace of the abutting sternum halves;

(b) exposing the split halves of the sternum;

(c) threading the surgical needle portion of the band assembly through the intercostal tissue along the outer edge of the first half of the sternum;

(d) further threading the surgical needle of the banding assembly through the intercostal tissue along the outer edge of the second half of the sternum so that a sufficient working length of the band has been drawn through;

(e) removing the surgical needle from the band;

(f) inserting the diminished width portion of the band through the buckle band guide and retaining slide through course so that the intermediate portion of the band passes through the buckle and a closed loop is formed;

(g) gripping the wider width portion of the band with a first surgical implement having jaws;

(h) gripping the buckle member using a second surgical implement having a pair of jaw tips, said gripping being achieved by positioning the jaw tips of the second surgical implement in the jaw tip receiving means of the buckle holding means;

(i) holding the buckle member with the second surgical implement;

(j) pulling the wider width portion of the band in the draw tight direction so that with the sternum halves proximated in abutment with the other, the closed loop is drawn into a tight compressive interengagement against the sternum halves to effect abutted closure thereof, and the loop locking means being operable to loop lock the band within the buckle member preventing any movement thereof, and sustaining set the looped compressive embrace of the abutting sternum halves; and (k) applying a pull-up force on the band portion near to and extending beyond the end of the buckle in the draw loop tight direction, so that the transversely weakened structure under the drawn tight end of the buckle on which the pull-up force is applied, frangibly separates from the drawn tight end of the buckle, as to leave no appreciable remainder band length beyond the buckle end, thereby avoiding sharp edged structure protrusion from the closed clamp loop.

22. The method of claim 21 in which step (h) comprises gripping the buckle member using a towel clamp, by positioning the jaw tips of the towel clamp tip receiving means of the buckle holding means.

23. The method of claim 22 in which step (g) comprises gripping the wider width portion of the band between the jaws of a Kocher clamp.

* * * * *